(12) United States Patent
Hong

(10) Patent No.: US 11,749,402 B2
(45) Date of Patent: Sep. 5, 2023

(54) METHOD AND SYSTEM FOR MULTI-MEDICAL DEPARTMENT SELECTION AND POST-MONITORING DURING TELEMEDICINE BASED ON PATIENT GENERATED HEALTH DATA (PGHD) AND DNA ANALYSIS DATA

(71) Applicant: LEMONHEALTHCARE LTD, Seoul (KR)

(72) Inventor: Byung Jin Hong, Seoul (KR)

(73) Assignee: LEMONHEALTHCARE LTD, Seoul (KR)

( * ) Notice: Subject to any disclaimer, the term of this patent is extended or adjusted under 35 U.S.C. 154(b) by 0 days.

(21) Appl. No.: 17/928,950

(22) PCT Filed: Jun. 17, 2021

(86) PCT No.: PCT/KR2021/007622
§ 371 (c)(1),
(2) Date: Dec. 1, 2022

(87) PCT Pub. No.: WO2021/256877
PCT Pub. Date: Dec. 23, 2021

(65) Prior Publication Data
US 2023/0197258 A1    Jun. 22, 2023

(30) Foreign Application Priority Data

Jun. 18, 2020   (KR) .................. 10-2020-0074342

(51) Int. Cl.
*G16H 40/20*   (2018.01)
*G16H 80/00*   (2018.01)
(Continued)

(52) U.S. Cl.
CPC ............. *G16H 40/20* (2018.01); *G16H 10/20* (2018.01); *G16H 40/67* (2018.01); *G16H 50/70* (2018.01); *G16H 80/00* (2018.01); *H04L 63/08* (2013.01)

(58) Field of Classification Search
CPC ........ G16H 40/20; G16H 10/20; G16H 40/67; G16H 50/70; G16H 80/00; H04L 63/08
(Continued)

(56) References Cited

U.S. PATENT DOCUMENTS

2017/0011210 A1 *  1/2017  Cheong .................. A61B 5/681
2018/0001184 A1 *  1/2018  Tran ....................... G16H 50/20
2019/0295096 A1 *  9/2019  Kim ........................ G06F 3/0362

FOREIGN PATENT DOCUMENTS

JP     2019-212264 A     12/2019
JP     2019212264 A   *  12/2019
(Continued)

OTHER PUBLICATIONS

Basilakis et al., "Design of a Decision-Support Architecture for Management of Remotely Monitored Patients," in IEEE Transactions on Information Technology in Biomedicine, vol. 14, No. 5, pp. 1216-1226, Sep. 2010, doi: 10.1109/TITB.2010.2055881. (Year: 2010 ).*

*Primary Examiner* — Joy Chng
(74) *Attorney, Agent, or Firm* — NKL Law; Byungwoong Park

(57) ABSTRACT

Proposed is a method of selecting and post-monitoring a multi-medical care department during telemedicine based on patient generated healthcare data (PGHD) and DNA analysis data. The method includes: performing user authentication based on personal information received from a user terminal when the user terminal executes a dedicated application and requests a telemedicine service from the cloud server, and requesting the telemedicine service from the hospital server (Continued)

when the user authentication is completed; setting the telemedicine service, transmitting a setting completion message to the cloud server when the setting is completed, and transmitting a telemedicine service approval message to the user terminal; collecting health measurement data including the PGHD, patient's DNA analysis data, and preliminary examination/medical inquiry questionnaire data, and transmitting the collected health measurement data to the cloud server; and analyzing the received health measurement data.

5 Claims, 4 Drawing Sheets

(51) Int. Cl.
  G16H 40/67 (2018.01)
  G16H 50/70 (2018.01)
  H04L 9/40 (2022.01)
  G16H 10/20 (2018.01)

(58) Field of Classification Search
  USPC ............................................. 705/2–3
  See application file for complete search history.

(56) References Cited

FOREIGN PATENT DOCUMENTS

| KR | 10-2014-0042388 A | 4/2014 | |
|---|---|---|---|
| KR | 10-2016-0026257 A | 3/2016 | |
| KR | 10-2017-0106942 A | 9/2017 | |
| KR | 10-2018-0040300 A | 4/2018 | |
| KR | 10-1927373 B1 | 12/2018 | |
| KR | 1927373 B1 * | 12/2018 | ......... G08B 21/0277 |
| KR | 10-2019-0006754 A | 1/2019 | |

* cited by examiner

METHOD AND SYSTEM FOR MULTI-MEDICAL DEPARTMENT SELECTION AND POST-MONITORING DURING TELEMEDICINE BASED ON PATIENT GENERATED HEALTH DATA (PGHD) AND DNA ANALYSIS DATA

CROSS REFERENCE TO RELATED APPLICATION

The present application is a national stage of PCT/KR2021/007622 filed Jun. 17, 2021, which claims priority to Korean Patent Application No. 10-2020-0074342, filed Jun. 18, 2020, the entire contents of which are incorporated herein for all purposes by this reference.

BACKGROUND

Technical Field

The present disclosure relates to a method and system for selecting and post-monitoring a multi-medical care department during telemedicine based on PGHD and DNA analysis data, and more particularly, to a method and system for selecting and post-monitoring a multi-medical care department during telemedicine based on PGHD and DNA analysis data capable of recommending an appropriate medical care department in real time and post-monitoring after a medical care by analyzing patient's PGHD, patient's DNA analysis data, and preliminary examination/medical inquiry questionnaire data upon requesting telemedicine.

Background Art

Since telemedicine has problems in that the quality of medical care may not be guaranteed, legal responsibility may be unclear, and the like according to medical care results, although the telemedicine has many advantages, its introduction is on hold. However, the need for telemedicine is emerging due to the recent spread of infectious diseases, and the government's approval of telemedicine is actually becoming visible.

However, in the case of the telemedicine, in general, there is a problem in that patients simply select a medical care department they want to directly take medical care from and take medical care.

The related art includes Patent Publication No. 10-2018-0040300 (Device and method for processing medical data to support remote diagnosis), but the related art discloses technology that utilizes medical care opinions acquired from consulting doctors by performing telemedicine for patients and uses these opinions for medical care to provide medical care-related advice and education services.

SUMMARY

The present disclosure provides a method and system for selecting and post-monitoring a multi-medical care department during telemedicine based on patient generated healthcare data (PGHD) and DNA analysis data capable of recommending a medical care department in real time and performing post-monitoring after medical care by analyzing the PGHD, patient's DNA analysis data, and preliminary examination/medical inquiry questionnaire data so that a patient can take multi-medical care by analyzing whether multi-medical care department reservations are necessary as well as a medical care department requested by a patient.

In an aspect, a method of selecting and post-monitoring a multi-medical care department during telemedicine based on patient generated healthcare data (PGHD) and DNA analysis data includes: performing, by a cloud server, user authentication based on personal information received from a user terminal when the user terminal executes a dedicated application and requests a telemedicine service from the cloud server, and requesting, by the cloud server the telemedicine service from the hospital server when the user authentication is completed; setting, by a hospital server, the telemedicine service, transmitting a setting completion message to the cloud server when the setting is completed, and transmitting, by the cloud server, a telemedicine service approval message to the user terminal; collecting, by the user terminal, health measurement data including the PGHD, patient's DNA analysis data, and preliminary examination/medical inquiry questionnaire data, and transmitting the collected health measurement data to the cloud server; and analyzing, by the cloud server, the received health measurement data.

According to the present disclosure, it is possible to perform medical care by determining abnormal signs of PGHD, genome (DNA) analysis, and preliminary examination/medical inquiry questionnaire data during telemedicine, calling a related medical care department multiple times, and implementing collaborative medical care within remote medical means to detect patients' diseases and conditions at an early stage.

In addition, it is possible to check a patient's abnormal health condition in real time by monitoring PGHD even after medical care.

In addition, it is possible to provide a recommendation service to patients who require medical care in a specific department.

DESCRIPTION OF EXEMPLARY EMBODIMENTS

Specific structural or functional descriptions disclosed in the present specification will be provided only in order to describe exemplary embodiments of the present disclosure. Therefore, exemplary embodiments of the present disclosure may be implemented in various forms, and the present disclosure is not to be interpreted as being limited to exemplary embodiments described in the present specification.

Since exemplary embodiments of the present disclosure may be variously modified and may have several forms, they will be shown in the accompanying drawings and be described in detail in the present specification. However, it is to be understood that exemplary embodiments of the present disclosure are not limited to specific forms, but includes all modifications, equivalents, and substitutions included in the spirit and the scope of the present disclosure.

Terms used in the present specification are used only in order to describe specific exemplary embodiments rather than limiting the present disclosure. Singular forms are intended to include plural forms unless the context clearly indicates otherwise. It is to be understood that terms "include," "have." or the like, used in the present specification specify the presence of features, numerals, steps, operations, components, parts, or a combination thereof stated in the present specification, but do not preclude the presence or addition of one or more other features, numerals, steps, operations, components, parts, or a combination thereof.

Hereinafter, embodiments of the present disclosure will be described in detail with reference to the accompanying drawings.

Figure 1:
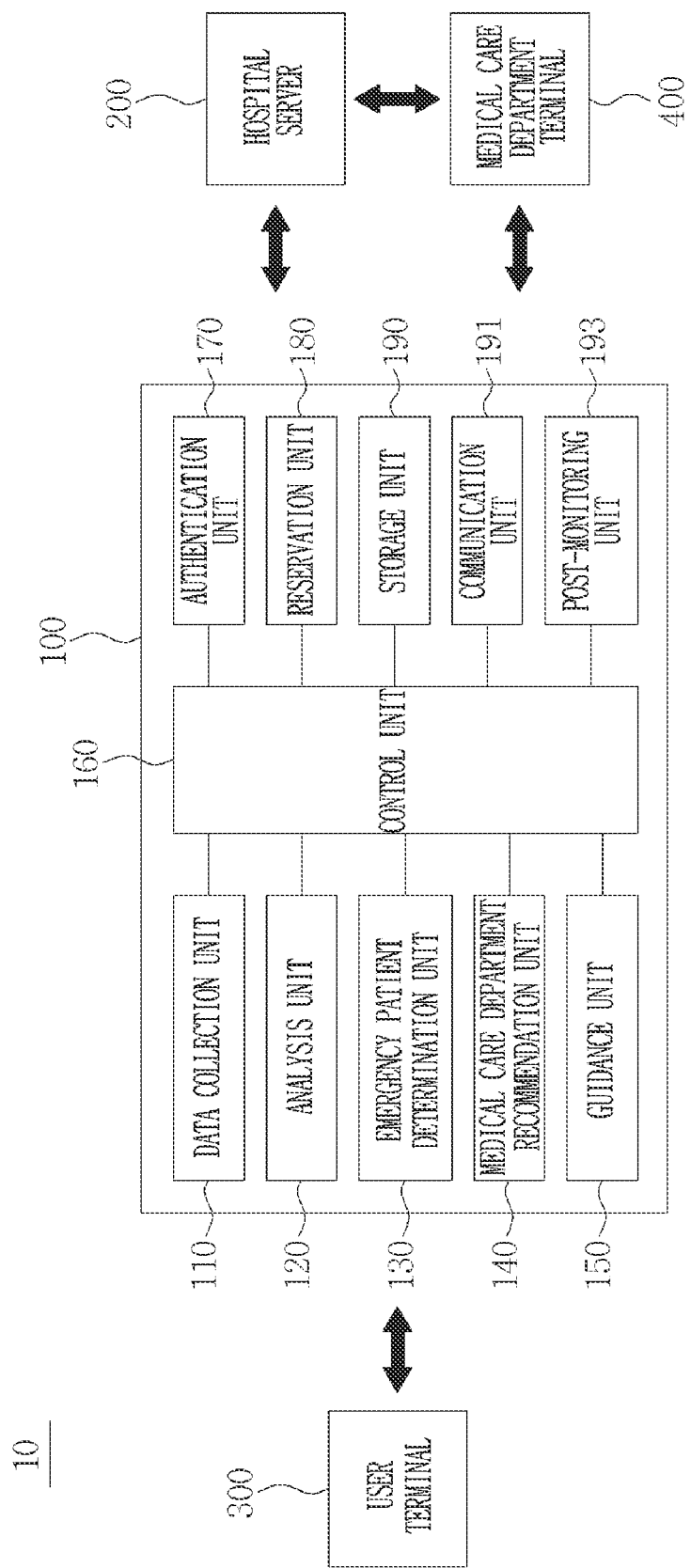
FIG. 1 is a configuration diagram of a method and system for selecting and post-monitoring a multi-medical care department during telemedicine based on patient generated healthcare data (PGHD) and DNA analysis data.

FIG. 1 is a configuration diagram of a method and system for selecting and post-monitoring a multi-medical care department during telemedicine based on patient generated healthcare data (PGHD) and DNA analysis data.

Referring to FIG. 1, a system 10 for selecting and post-monitoring a multi-medical care department includes a cloud server 100, a hospital server 200, a user terminal 300, and a medical care department terminal 400.

The cloud server 100 includes a data collection unit 110, an analysis unit 120, an emergency patient determination unit 130, a medical care department recommendation unit 140, a guidance unit 150, a control unit 160, an authentication unit 170, a reservation unit 180, a storage unit 190, a communication unit 191, and a post-monitoring unit 193.

The data collection unit 110 receives health measurement data including patient generated healthcare data (PGHD), patient's DNA analysis data, and preliminary examination/medical inquiry questionnaire data from a user terminal. In addition, it is possible to collect basic data for training a medical care department recommendation model for training based on deep learning.

The analysis unit 120 may analyze health measurement data received from the user terminal. The analysis unit 120 may pre-process the received health measurement data. The analysis unit 120 may convert the collected health measurement data into categorical data and assign a weight to the converted categorical data. The analysis unit 120 may standardize and normalize weighted data.

The emergency patient determination unit 130 determines whether a patient is an emergency patient based on the health measurement data analyzed by the analysis unit, and notifies the hospital server 200 and the user terminal 300 of the emergency patient when it is determined that the patient is the emergency patient.

The medical care department recommendation unit 140 analyzes recommended medical care departments based on the health measurement data received from the user terminal. In this case, the medical care department recommendation unit 140 may pre-process the health measurement data and classify medical care departments requiring medical care based on the previously trained medical care department recommendation model. It is possible to extract the medical care department requiring the medical care by classifying patient generated healthcare data (PGHD), DNA analysis data, and preliminary examination/medical inquiry questionnaire data that re included in the health measurement data, and inputting the PGHD, the DNA analysis data, and the preliminary examination/medical inquiry questionnaire data to the medical care departments. The medical care department recommendation unit 140 may recommend the extracted medical care department to the user terminal 300.

When the guidance unit 150 receives a multi-medical care department reservation completion message and a single medical care department reservation completion message from a hospital server, the guidance unit notifies the user terminal of the reservation completion message.

The control unit 160 controls each component of the cloud server.

Upon receiving a telemedicine service request from the user terminal, the authentication unit 170 performs user authentication based on personal information received from the user terminal.

When the reservation unit 180 receives the medical care department reservation request from the user terminal, the reservation unit 180 checks availability of reservation to the hospital server 200. Upon receiving the reservation completion information from the hospital server, the reservation completion information is notified to the user terminal.

The storage unit 190 receives health measurement data collected from the user terminal, classifies the PGHD for each patient, and stores the classified PGHD in the storage unit.

The communication unit 191 may transmit and receive data to and from the hospital server 200 and the user terminal 300.

The post-monitoring unit 193 may periodically receive and monitor the PGHD from the user terminal after the medical care is terminated, and transmit a notification notifying an abnormal health condition to the user terminal 300 when a data change greater than a reference value occurs in the PGHD during monitoring. According to an embodiment, the notification may be transmitted to the hospital server 200.

The hospital server 200 may perform post-monitoring based on the PGHD after the medical care is terminated. If there is a data change greater than a reference value during monitoring, the hospital server 200 transmits a notification notifying the abnormal health condition to the medical care department terminal. According to an embodiment, the hospital server 200 may transmit a notification to the user terminal 300. The hospital server gathers the PGHD and monitors a trend of data, but if there is the data change greater than the reference value, the hospital server transmits a notification notifying the abnormal health condition to the multi-medical care department.

Figure 2:
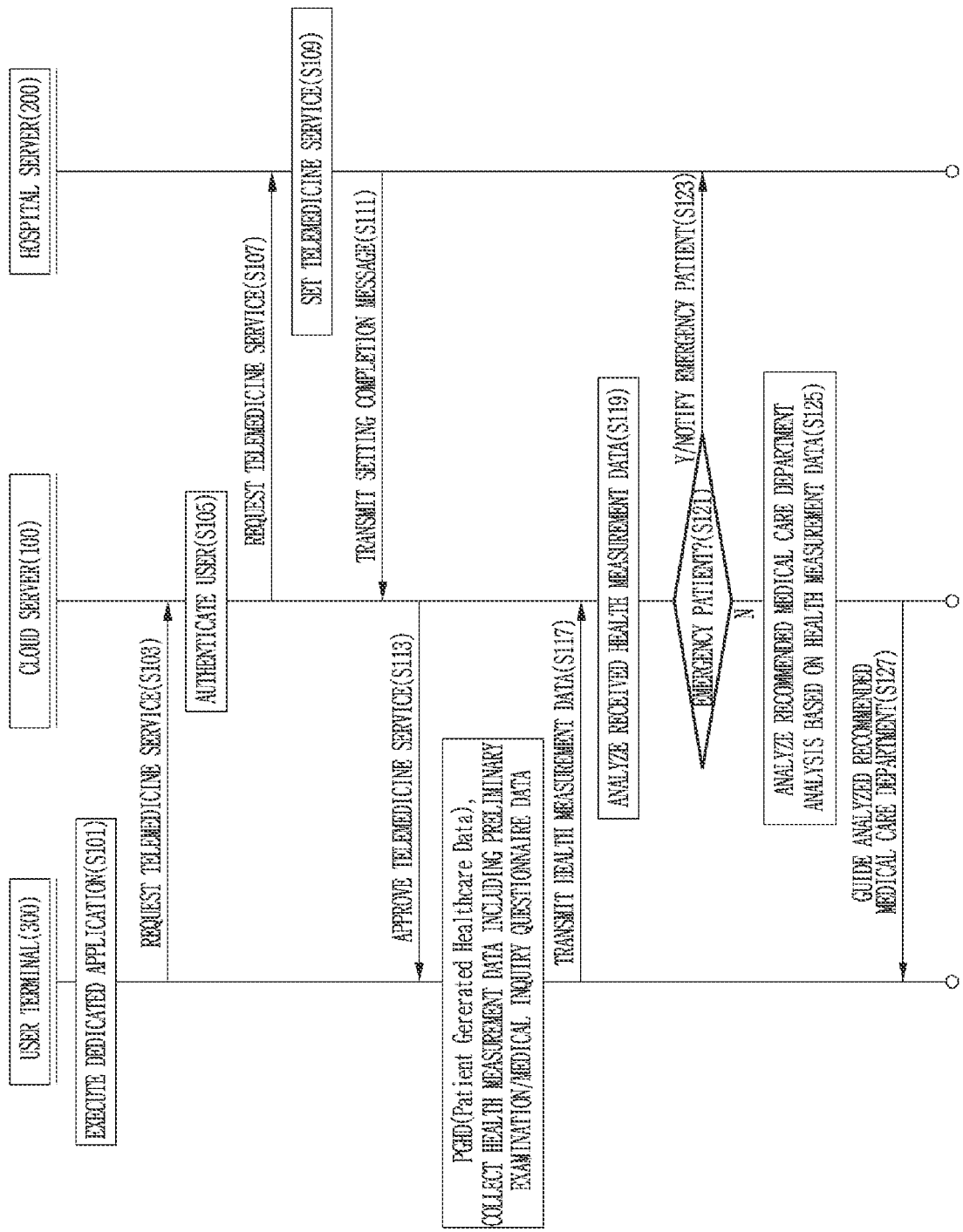
FIG. 2 is a flowchart illustrating a method of selecting and post-monitoring a multi-medical care department during telemedicine based on patient generated healthcare data (PGHD) and DNA analysis data according to an embodiment of the present disclosure.
Figure 3:
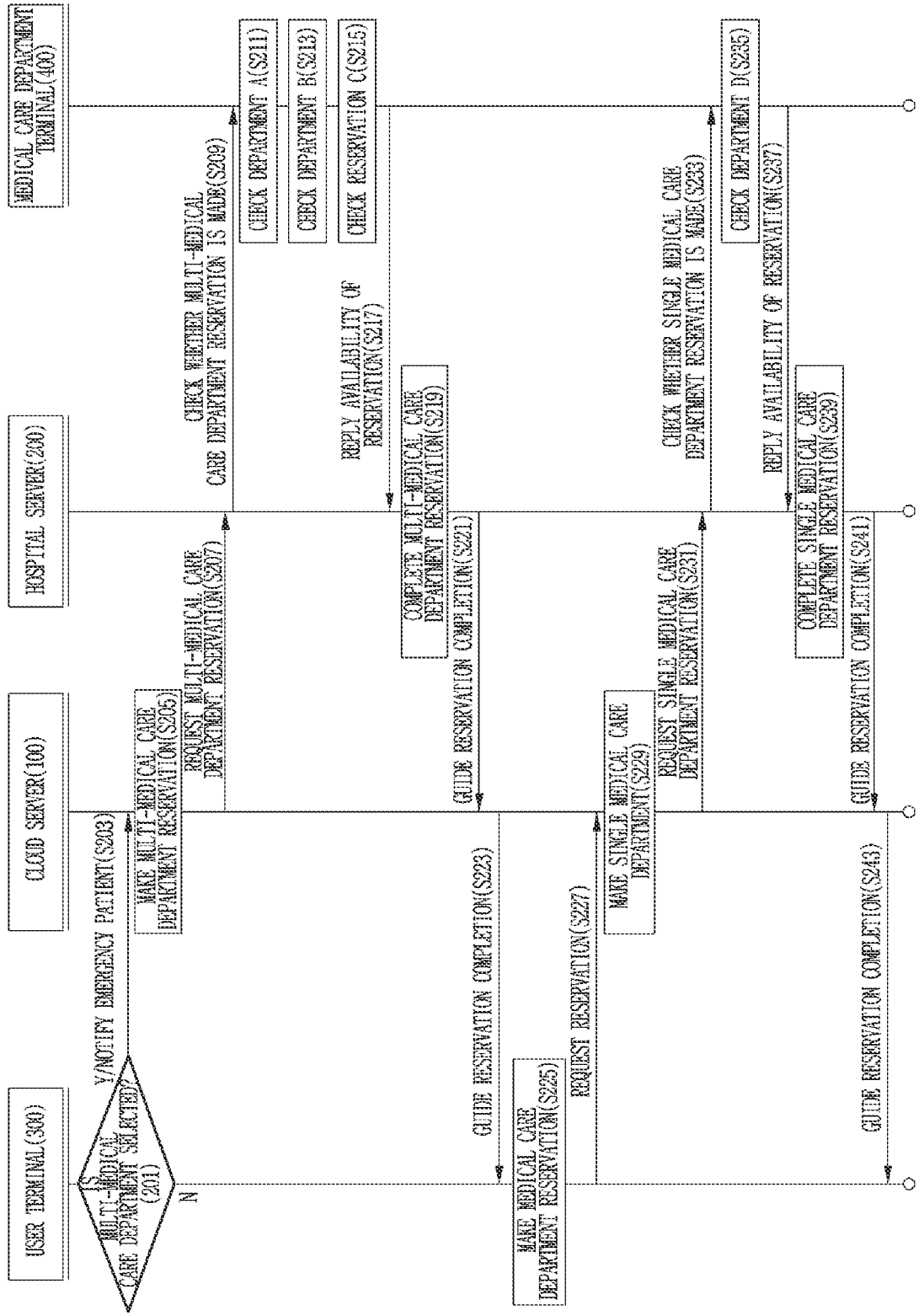
FIG. 3 is a flowchart illustrating a method of selecting and post-monitoring a multi-medical care department during telemedicine based on patient generated healthcare data (PGHD) and DNA analysis data according to an embodiment of the present disclosure.
Figure 4:
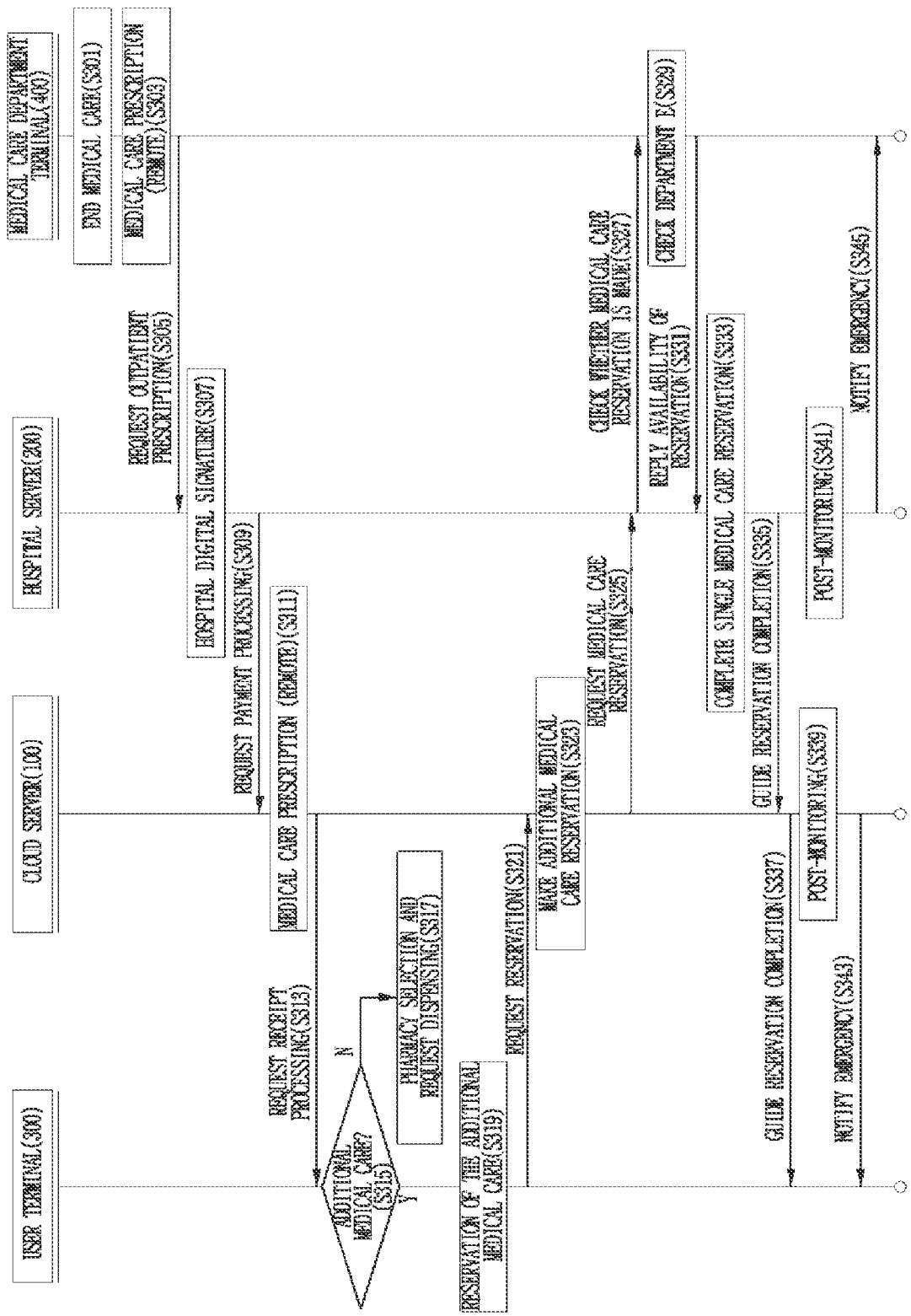
FIG. 4 is a flowchart illustrating a method of selecting and post-monitoring a multi-medical care department during telemedicine based on patient generated healthcare data (PGHD) and DNA analysis data according to an embodiment of the present disclosure.

FIGS. 2 to 4 are flowcharts illustrating a method of selecting and post-monitoring a multi-medical care department during telemedicine based on patient generated healthcare data (PGHD) and DNA analysis data according to an embodiment of the present disclosure.

Referring to FIG. 2, the user terminal 300 executes a dedicated application (S101) and requests a telemedicine service from the cloud server 100 (S103). The cloud server 100 performs user authentication based on the personal information received from the user terminal (S105).

When the user authentication is completed, the cloud server 100 requests a telemedicine service from the hospital server 200 (S107). The hospital server 200 performs settings for the telemedicine service, and when the settings are completed, transmits a setting completion message to the cloud server 100 (S111). The cloud server 100 transmits a telemedicine service approval message to the user terminal 300 (S113).

The user terminal 300 collects health measurement data including the PGHD, the patient's DNA analysis data, and the preliminary examination/medical inquiry questionnaire data (S115). The PGHD may be at least one of blood pressure, blood sugar, body weight, body temperature, activity level, and electrocardiogram.

The user terminal 300 interworks with a plurality of wearable devices or home care devices using the using an artificial intelligence speaker as a hub, or interworks with blood pressure, pulse, electrocardiogram, oxygen saturation, etc. measured by a smartphone without the wearable device, and the artificial intelligence speaker collects data and transmits the collected data to the cloud server 100. The user terminal transmits the PGHD to a cloud server through a plurality of wearable devices, home care devices, and smart phones that measure the PGHD, and the cloud server transmits the PGHD to the hospital server.

The user terminal 300 transmits the collected health measurement data to the cloud server (S117). The cloud server 100 receives the health measurement data collected from the user terminal, classifies the PGHD for each patient, and stores the classified PGHD in the storage unit.

The cloud server 100 analyzes the received health measurement data (S119). The cloud server 100 determines whether a patient is an emergency patient according to the result of analyzing the health measurement data (S121).

When the cloud server 100 is determined to be an emergency patient according to the analysis result, the cloud server 100 notifies the hospital server 200 of the emergency patient in real time (S123). When the cloud server 100 is not determined to be the emergency patient according to the analysis result, the cloud server 100 analyzes the recommended medical care department based on the health measurement data (S125).

The cloud server 100 guides the analyzed recommended medical care department to the user terminal 300 (S127).

Referring to FIG. 3, when the user terminal 300 requests a reservation from the cloud server when the medical care department recommended by the cloud server 100 is a multi-medical care department (S203), the cloud server 100 request a multi-medical care department reservation from the hospital server 200 (S207), and the hospital server 200 checks availability of reservation to a plurality of multi-medical care department terminals 400 (S209). A plurality of medical care department terminals check availability of reservation (S211 to S215), and reply the availability to the hospital server 200. The hospital server 200 completes the multi-medical care department reservation according to the reply result (S219), and informs the cloud server of the reservation completion (S221). The cloud server 100 informs the user terminal 300 of the reservation completion (S223).

When the medical care department recommended by the cloud server 100 is a single medical care department, the user terminal 300 reserves a single medical care department (S225). When a reservation request is made to the cloud server (S227), the cloud server 100 makes a single medical care department reservation request to the hospital server 200 (S231), and the hospital server 200 checks availability of reservation to the single medical care department terminal 400 (S233). The single medical care department terminal checks availability of reservation (S233), and returns the availability to the hospital server 200 (S237). The hospital server completes the single medical care department reservation according to the reply result (S239), and guides the cloud server of the reservation completion (S241). The cloud server 100 informs the user terminal 300 of the reservation completion (S243).

Referring to FIG. 4, when the medical care department terminal 400 terminates the medical care (S301), the medical care department terminal 400 requests a medical care prescription (S303). The medical care department terminal 400 requests an outpatient prescription from the hospital server 200 (S305), and the hospital server 200 performs the hospital digital signature (S307). The hospital server 200 requests payment processing from the cloud server 100, and the cloud server 100 issues the medical care prescription (S311).

The cloud server 100 requests receipt processing from the user terminal 300 (S313), the user terminal determines whether additional medical care is required (S315), and performs a pharmacy selection and dispensing request if additional medical care is not performed (S317). When the user terminal 300 performs the additional medical care, the user terminal 300 requests the reservation of the additional medical care (S321), and the cloud server 100 reserves the additional medical care (S323). The cloud server 100 requests a medical care department reservation from the hospital server 200 (S325), the hospital server 200 checks the availability of the medical care department reservation to the medical care department terminal 400 (S327), the medical care department terminal checks the availability of reservation (S329), and replies the availability to the hospital server 200 (S331). The hospital server completes the single medical care department reservation according to the reply result (S333). The hospital server guides the reservation completion to the cloud server (S335). The cloud server 100 guides the reservation completion to the user terminal 300 (S337).

The cloud server 100 and the hospital server 200 perform the post-monitoring based on the collected health measurement data (S339 and S341).

When the data change greater than the reference value occurs in the PGHD during the monitoring by the cloud server 100, a notification notifying an abnormal health condition is transmitted to the user terminal (S339). According to an embodiment, the cloud server 100 may transmit a notification to the hospital server 200.

When the data change greater than the reference value occurs in the PGHD during the monitoring, the hospital server 200 transmits the notification notifying the abnormal health condition to the medical care department terminal (S339). According to an embodiment, the hospital server 200 may transmit a notification to the user terminal 300. The hospital server performs real-time remote monitoring based on artificial intelligence according to the received PGHD, but transmits a notification notifying the abnormal health condition to the user terminal when the data change greater than the reference value occurs in the PGHD. The hospital server gathers the PGHD and monitors a trend of data, but if there is the data change greater than the reference value, the hospital server transmits a notification notifying the abnormal health condition to the multi-medical care department.

The cloud server 100 may notify a telemedicine patient to receive medical care by making a recommendation and request to the telemedicine patient when analysis of genetic information such as DNA and additional PHR data measurement and information analysis are required.

When the abnormal health condition is checked during the monitoring, the cloud server 100 may provide emergency notification and proxy medical care reservations by providing abnormal condition information to terminals of designated targets (family members, social workers, local health centers, etc.) with patient consent.

Although the present disclosure has been described with reference to exemplary embodiments shown in the accompanying drawings, it is only an example. It will be understood by those skilled in the art that various modifications and equivalent other exemplary embodiments are possible from the present disclosure. Accordingly, an actual technical protection scope of the present disclosure is to be defined by the technical spirit of the following claims.

What is claimed is:

1. A method of selecting and post-monitoring a multi-medical care department during telemedicine based on patient generated healthcare data (PGHD) and DNA analysis data, the method comprising:

performing, by a cloud server, user authentication based on personal information received from a user terminal when the user terminal executes a dedicated application and requests a telemedicine service from the cloud server, and requesting, by the cloud server the telemedicine service from the hospital server when the user authentication is completed;

setting, by a hospital server, the telemedicine service, transmitting a setting completion message to the cloud server when the setting is completed, and transmitting, by the cloud server, a telemedicine service approval message to the user terminal;

collecting, by the user terminal, health measurement data including the PGHD, patient's DNA analysis data, and preliminary examination/medical inquiry questionnaire data, and transmitting the collected health measurement data to the cloud server;

analyzing, by the cloud server, the received health measurement data;

determining, by the cloud server, whether a patient is an emergency patient according to a result of analyzing the health measurement data and notifying the hospital server of the emergency patient in real time when it is determined that the patient is the emergency patient;

determining, by the cloud server, whether the patient is the emergency patient according to a result of analyzing the health measurement data and analyzing a recommended medical care department based on the health measurement data when it is determined that the patient is not the emergency patient;

guiding, by the cloud server, the analyzed recommended medical care department to the user terminal; and requesting, by the cloud server, a multi-medical care department reservation from the hospital server to make a reservation to the multi-medical care department and checking, by the hospital server, availability of reservations to a plurality of medical care department terminals, if a reservation is requested to the cloud server when the medical care department recommended by the user terminal is a multi-medical care department;

wherein the user terminal interlocks the PGHD with a plurality of wearable devices or home care devices using an artificial intelligence speaker as a hub, or measures and interlocks with a smartphone without the wearable device or the home care device, and the artificial intelligence speaker collects data and transmits the collected data to the cloud server, wherein the cloud server includes an analysis unit, a medical care department recommendation unit, and a post-monitoring unit, wherein the analysis unit convert the collected health measurement data into categorical data, and assign a weight to the converted categorical data, and standardize and normalize weighted data, wherein the medical care department recommendation unit pre-process the health measurement data, and classify medical care departments requiring medical care based on the previously trained medical care department recommendation model, and extract the medical care department requiring the medical care by classifying patient generated healthcare data (PGHD), DNA analysis data, and preliminary examination/medical inquiry questionnaire data that re included in the health measurement data, and inputting the PGHD, the DNA analysis data, and the preliminary examination/medical inquiry questionnaire data to the medical care departments, wherein the post-monitoring unit periodically receive and monitor the PGHD from the user terminal after the medical care is terminated, and transmit a notification notifying an abnormal health condition to the user terminal when a data change greater than a reference value occurs in the PGHD during monitoring.

2. The method of claim 1, wherein the user terminal transmits the PGHD to the cloud server through a plurality of wearable devices or home care devices that measure the PGHD, and the cloud server transmits the PGHD to the hospital server.

3. The method of claim 2, wherein the hospital server performs real-time remote monitoring based on based on artificial intelligence according to the received PGHD, but transmits a notification notifying the abnormal health condition to the user terminal when a data change greater than a reference value occurs in the PGHD.

4. The method of claim 2, wherein the hospital server gathers the PGHD, monitors a trend of data, and transmits a notification notifying the abnormal health condition to the multi-medical care department when the data change greater than the reference value occur.

5. The method of claim 1, wherein the cloud server receives the health measurement data collected from the user terminal, classifies the PGHD for each patient, and stores the classified PGHD in the storage unit.

* * * * *